(12) United States Patent
Zhang et al.

(10) Patent No.: US 12,144,735 B2
(45) Date of Patent: Nov. 19, 2024

(54) ARTIFICIAL ACETABULAR CUP AND MANUFACTURING METHOD THEREOF

(71) Applicants: b-ONE Medical (Suzhou) Co., Ltd., Jiangsu (CN); b-ONE Medical Biotech Corporation, Wuxi (CN); b-ONE Ortho, Corp, Cedar Knolls, NJ (US)

(72) Inventors: Zongtao Zhang, Cedar Knolls, NJ (US); Imants Liepins, Cedar Knolls, NJ (US); Michael Lowry, Cedar Knolls, NJ (US)

(73) Assignees: b-ONE MEDICAL (SUZHOU) CO., LTD., Suzhou (CN); b-ONE Medical Biotech Corporation, Wuxi (CN); b-ONE Ortho, Corp, Cedar Knolls, NJ (US)

( * ) Notice: Subject to any disclaimer, the term of this patent is extended or adjusted under 35 U.S.C. 154(b) by 938 days.

(21) Appl. No.: 17/160,368

(22) Filed: Jan. 27, 2021

(65) Prior Publication Data
US 2022/0233319 A1    Jul. 28, 2022

(51) Int. Cl.
*A61F 2/34* (2006.01)
*A61F 2/30* (2006.01)
*A61F 2/46* (2006.01)

(52) U.S. Cl.
CPC ............ *A61F 2/34* (2013.01); *A61F 2/30942* (2013.01); *A61F 2/4609* (2013.01); *A61F 2002/30985* (2013.01); *A61F 2002/342* (2013.01); *A61F 2002/3479* (2013.01); *A61F 2310/00023* (2013.01); *A61F 2310/00029* (2013.01)

(58) Field of Classification Search
CPC .................. A61F 2/34; A61F 2002/342; A61F 2002/3425; A61F 2002/3479
See application file for complete search history.

(56) References Cited

U.S. PATENT DOCUMENTS

| | | | | |
|---|---|---|---|---|
| 5,019,083 | A  * | 5/1991 | Klapper | A61F 2/4607 606/86 R |
| 8,066,778 | B2 * | 11/2011 | Meridew | A61F 2/4609 623/22.32 |
| 2009/0105772 | A1 | 4/2009 | Seebeck et al. | |
| 2015/0018956 | A1 | 1/2015 | Steinmann et al. | |

* cited by examiner

Primary Examiner — Brian A Dukert
(74) Attorney, Agent, or Firm — HSML P. C.

(57) ABSTRACT

The application discloses an artificial acetabular cup and a manufacturing method thereof. The artificial acetabular cup has an annular base and a dome extending from the annular base. At least a part of the inner layer of the dome is a solid layer, at least a part of the outer layer of the dome is a porous structure layer, and the thickness of the inner layer is less than that of the porous structure layer. The artificial acetabular cup of the present application has lower production cost and better performance.

13 Claims, 6 Drawing Sheets

ARTIFICIAL ACETABULAR CUP AND MANUFACTURING METHOD THEREOF

TECHNICAL FIELD

The present invention relates to the field of medical devices, in particular to orthopedic implants.

BACKGROUND OF THE INVENTION

Artificial hip joints usually comprise an artificial acetabular cup to be fixed to the upper limb of a human body, a hemispherical plastic part mounted in the artificial acetabular cup, and a ball head fixed to the lower limb of the human body by a fastener. The existing artificial acetabular cup usually comprises a solid metal seat and a solid metal dome extending from the solid metal seat. The outer layer of the dome of some existing artificial acetabular cups is also covered with a porous structure layer.

The inventor of the present application found that, since the solid metal part is too thick, when a force is applied to the existing artificial acetabular cup, most of the force will be absorbed by the solid metal part and is difficult to be transmitted to the bones of the human body, resulting in very little force stimulation, or even no force stimulation to the human bones. And when there is no or very little force stimulation to the human bones, the bones will stop growing. Therefore, it is necessary to develop a better artificial acetabular cup.

The inventor of the present application also found that, in the existing orthopedic implants, portions in contact with the human bones are still difficult to match with the human bones, and not able to promote the bones growing well. Therefore, there is a need to develop better orthopedic implant structures.

SUMMARY OF THE INVENTION

An object of the present invention is to provide an artificial acetabular cup with better performance.

In order to achieve the above object, the present invention provides an artificial acetabular cup having an annular base and a dome extending from the annular base, wherein the dome has an inner layer and an outer layer covering the inner layer, at least a part of the inner layer of the dome is a solid layer, at least a part of the outer layer of the dome is a porous structure layer, and the thickness of the inner layer is less than that of the porous structure layer.

In an embodiment, the inner layer of the dome has a plurality of solid beams extending between the annular base and the top of the dome in the longitude direction, the plurality of solid beams is spaced apart from each other in the latitude direction, and a porous structure is arranged between two adjacent solid beams, and the outer surface of the dome is provided with a porous structure.

In an embodiment, at least a part of the inner layer of the dome is a porous layer, and the porous layer portion of the inner layer of the dome is concave relative to the solid beam.

In an embodiment, the entire inner layer of the dome is a solid layer.

In an embodiment, the entire outer layer of the dome is a porous structure layer.

In an embodiment, the thickness of the inner layer is $1/50 \sim 1/2$ of that of the outer layer.

In an embodiment, at least one of the solid beams is provided with a mounting hole.

In an embodiment, the dome has a solid cylindrical portion integrally extending from the upper end surface of the annular base and a plurality of solid beams extending from the solid cylindrical portion in the longitudinal direction.

In an embodiment, the inner side edge of the annular base is provided with a plurality of opening grooves spaced apart in the latitude direction that is open to the inner side of the dome.

In an embodiment, the outer surface of the outer layer of the dome is distributed with spikes.

In an embodiment, the spike is integrally formed on the outer surface of the outer layer of the dome.

In an embodiment, the distance between two adjacent spikes is 300 μm 1000 μm.

In an embodiment, the angle between the central axis of the spike and the tangent to the outer surface of the outer layer of the dome is 65°~110°.

In an embodiment, the outer surface of the outer layer of the dome is arcuate surface. Preferably, the outer surface of the outer layer of the dome is a spherical surface.

In an embodiment, the artificial acetabular cup is formed by 3D printing.

In an embodiment, the artificial acetabular cup is made of titanium alloy, pure titanium, cobalt-chromium alloy, or stainless steel.

According to another aspect of the present application, there is provided a manufacturing method of an artificial acetabular cup, comprising the following steps:

S1. building a digital model of an artificial acetabular cup, which has an annular base and a dome extending from the annular base, at least a part of the inner layer of the dome is a solid layer, and at least a part of the outer layer of the dome is a porous structure layer, and the thickness of the inner layer is less than that of the porous structure layer;

S2. 3D printing the digital model of the artificial acetabular cup.

In an embodiment, the step S1 comprises the following sub-steps:

S11. building a digital model of a porous substrate and a digital model of a solid substrate;

S12. adding a digital model of spike to the digital model of the porous substrate, resulting in the digital model of the spike and the digital model of the porous substrate overlapping;

S13. arraying the digital model of the spike to obtain a plurality of digital models of the spike;

S14. merging the plurality of digital models of the spike obtained by arraying with the digital model of the porous substrate, and merging the digital model of the porous substrate with the digital model of the solid substrate.

In an embodiment, the manufacturing method further comprises the following steps: before performing 3D printing, further merging a digital model with a digital model of a porous foam, wherein the digital model is obtained by merging the plurality of the digital models of the spike obtained by arraying with the digital model of the porous substrate.

In an embodiment, the merging of the plurality of the digital models of the spike obtained by arraying with the digital model of the porous substrate is performed by Boolean operation.

In an embodiment, the step S1 comprises: cutting grooves on the outer surface of the porous structure of the outer layer to obtain spikes, and controlling the thickness and height of the spikes by adjusting the pitch and the depth of the grooves.

The present application also provides an artificial acetabular cup having an annular base and a dome extending from the annular base, wherein the dome is entirely porous structure layer.

In an embodiment, the inner side edge of the annular base is provided with an opening groove that is open to the inner side of the dome.

In an embodiment, the outer surface of the outer layer of the dome is distributed with spikes.

In an embodiment, the spike is integrally formed on the outer surface of the outer layer of the dome.

In an embodiment, the distance between two adjacent spikes is 300 µm~1000 µm.

In an embodiment, the angle between the central axis of the spike and the tangent to the outer surface of the outer layer of the dome is 65°~110°.

In an embodiment, the outer surface of the outer layer of the dome is arcuate surface. Preferably, the outer surface of the outer layer of the dome is a spherical surface.

In an embodiment, the artificial acetabular cup is formed by 3D printing. In an embodiment, the artificial acetabular cup is formed of titanium alloy, pure titanium, cobalt-chromium alloy, or stainless steel.

The volume of the solid part of the artificial acetabular cup of the present application is minimized, while the porous part occupies most of the volume, and because of using 3D printing technology, the artificial acetabular cup with the same rigidity has a lighter weight, a lower 3D Printing cost (less powder usage and shorter printing time), and is more conducive to promote the growth of the human bones.

THE DETAILED DESCRIPTIONS OF THE PREFERRED EMBODIMENTS

Figure 1:
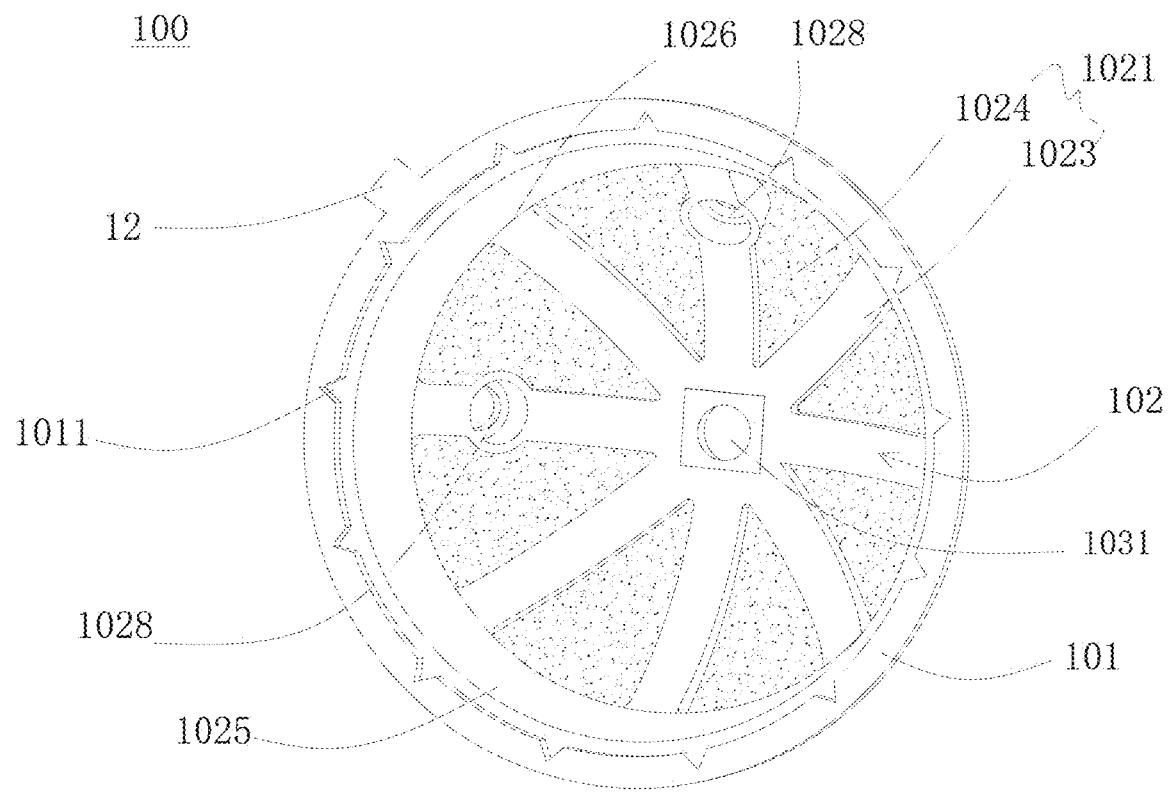
FIG. 1 is a perspective view of an artificial acetabular cup according to an embodiment of the present invention.

The preferred embodiments of the present invention will be described in detail below with reference to the accompanying drawings, so that the purposes, features and advantages of the present invention can be more clearly understood. It should be understood that the embodiments shown in the accompanying drawings are not intended to limit the scope of the present invention, and is only used for illustrating the essential spirit of the technical solution of the present invention.

In the following description, for the purpose of illustrating various disclosed embodiments, some specific details are set forth to provide a thorough understanding of various disclosed embodiments. However, those skilled in the relevant art will recognize that the embodiments may be embodied without one or more of these specific details. In other situations, well-known devices, structures, and technologies associated with the present application may not be shown or described in detail to avoid unnecessarily obscuring the description of the embodiments.

Unless the context has other requirement, throughout the specification and claims, the words "comprising" and its variations, such as "including" and "having" should be understood as open and inclusive meanings, that is, should be interpreted as "including, but not limited to".

Throughout the specification, reference to "one embodiment" or "an embodiment" means that a specific feature, structure, or characteristic described in combination with the embodiment is involved in at least one embodiment. Therefore, the appearances of "in one embodiment" or "in an embodiment" in various positions throughout the specification are not all refer to the same embodiment. In addition, specific features, structures, or characteristics may be combined in any manner in one or more embodiments.

As used in this specification and the appended claims, the singular forms "a" and "the" comprise plural referents unless the context clearly dictates otherwise. It should be noted that the term "or" is usually used in its meaning including "and/or", unless the context clearly stipulates otherwise.

In the following description, in order to clearly demonstrate the structure and working mode of the present invention, many directional words will be used for description, but the words "front", "rear", "left", "right", "outer", "inner", "outward", "inward", "upper", "lower" and other words should be understood as convenient terms and should not be understood as restrictive terms.

The present invention relates to orthopedic implants and manufacturing method thereof, in particular to artificial hip joints and manufacturing method thereof. Artificial hip joints usually comprises artificial acetabular cup, liner and a ball head. Artificial acetabular cup is used to be implanted into the acetabular of the pelvic cavity. and is usually made of titanium alloy or cobalt-chromium alloy. Liner is used as an interface of artificial hip joints, and is usually made of polyethylene, ceramic, metal, and etc. The ball head is joined to femoral stem through a fastener and cooperates with the liner to form a joint interface. The ball head is generally made of ceramic or metal materials. The present invention mainly relates to artificial acetabular cup. A large amounts of porous structures are used in the artificial acetabular cup. In particular, a large amounts of porous structures are used in the dome part of the artificial acetabular cup. Therefore, the weight of the artificial acetabular cup can be greatly reduced, production cost is lower, and the growth of the human bones are promoted.

Figure 2:
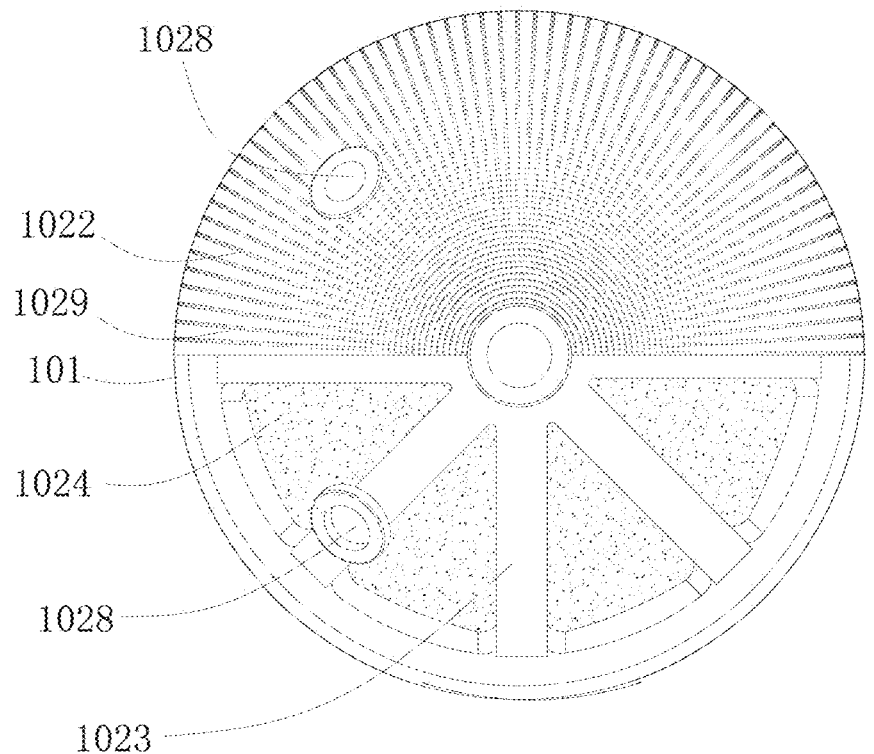
FIG. 2 is a top view of the artificial acetabular cup of FIG. 1 with some parts thereof removed.

FIGS. 1-2 show a structural diagram of an artificial acetabular cup 100 according to an embodiment of the present invention. As shown in FIGS. 1-2, the artificial acetabular cup 100 has an annular base 101 and a dome 102 integrally extending from the annular base 101. The inner diameter and outer diameter of the annular base 101 can be set according to different acetabular cup specifications to match the different acetabulum of the pelvic cavity of human bodies. The annular base 101 has a predetermined height, as long as meeting the demand of the strength, the lower the height, the better, so as to reduce the weight and production cost. In this application, the height H of the annular base 101 may be 10 mm to 40 mm. Preferably, the height H of the annular base 101 may be 19 mm to 38 mm.

The inner side edge of the annular base 101 is provided with a plurality of opening grooves 1011 spaced apart from each other in the latitude direction and open to the inner side of the dome 102. The shape of the opening groove 1011 matches with and can receive the outer peripheral edge of the corresponding artificial hip joint liner when assembling them together. In this embodiment, the radial cross section of opening groove 1011 is triangular. The outer side edge of the annular base 101 is also provided with a protruding piece 12 integrally extending outwardly from the outer side edge in the radial direction of the annular base 101 for holding during mounting.

The dome 102 integrally extends from the upper end surface of the annular base 101 and has a hemispherical shape. The dome 102 has an inner layer 1021 and an outer layer 1022 covering the inner layer 1021. The thickness of the inner layer 1021 is less than that of the outer layer 1022. The inner layer 1021 of the dome 102 comprises a solid layer 1023 and a porous structure layer 1024. The solid layer 1023 has a solid cylindrical portion 1025 integrally extending from the upper end surface of the annular base 101 and a plurality of solid beams 1026 extending from the solid cylindrical portion 1025 in the longitudinal direction. The plurality of solid beams 1026 are spaced apart from each other in the latitude direction. A porous structure 1024 is arranged between two adjacent solid beams 1026. The porous layer portion of the inner layer 1021 of the dome 102, that is, the porous structure 1024 is concave relative to the solid beam 1026. As a result, materials can be reduced. One or more mounting holes 1028 are provided in the solid beam 1026 for fixing the artificial acetabular cup to the human body. The top of the dome 102 is also provided with an assembling hole 1031, which is used to cooperate with corresponding tools when assembling the artificial acetabular cup to the human body. The solid portions provided with the mounting hole 1028 and the assembling hole 1031 respectively may be thicker than other solid portions, so that these solid portions have sufficient strength. It is understood that the above-mentioned solid beams 1026 may also directly extending from the upper end surface of the annular base 101 to the top of the dome 102, that is, the solid cylindrical portion 1025 can be cancelled. As a result, the amount of material can be further reduced.

The outer layer 1022 of the dome 102 integrally formed over the inner layer 1021. At least a part of the outer layer 1022 is a porous structure layer 1024. In this embodiment, except for the mounting holes and assembling holes, the rest of the outer layer 1022 is the porous structure layer 1024. In this case, the entire outer layer 1022 can be regarded as a porous structure layer 1024. The thickness of the inner layer 1021 is less than that of the outer layer 1022. The thickness T1 of the inner layer 1021 may be ⅟₅₀~½ of the thickness T2 of the outer layer 1022. Preferably, the thickness of the inner layer 1021 is 1/20 to 1/5 of the thickness of the outer layer 1022. In this application, since the thickness of the solid layer 1023 is less than the thickness of the porous structure layer 1024, the thickness of the solid metal portion is very thin, and can be as thin as 0.05 mm, when a force is applied to the acetabulum, the force is less blocked by the solid metal portion, and most of the force can be transmitted to the human bones, that is, the thinner solid metal portion can reduce the stress shielding to the acetabular bone, thereby stimulating the growth of the human bones, and then enabling the artificial acetabulum to better embed into the human body.

Furthermore, compared with the prior art wherein the thickness of the solid layer 1023 is much greater than that of the porous layer 1024, the weight of the acetabular cup of the present application can be greatly reduced, thereby greatly reducing the production cost. Table 1 below is a weight comparison of artificial acetabular cups made of titanium alloys with the same specifications and different structures. It can be seen that the total weight of the artificial acetabular cup in this application is only about ⅔ of that of the artificial acetabular cup in the prior art.

TABLE 1

| Sample No. | Characteristic | Weight | The reduced amount of Ti 6Al4V ELI powder |
|---|---|---|---|
| No. 1 controlled 50 mm shell | no beam, a porous layer with a thickness of 1.5 mm, a solid layer with a thickness of 3.5 mm, | 63.4 g | 0 |
| No. 2, 50 mm shell | having beam, a porous layer with a thickness of 4.0 mm, a solid layer with a thickness of 1.0 mm | 45.2 g | $\Delta W = -18.2$ g($\Delta$\$9.1/shell) |
| No. 3, 50 mm shell | having beam, a porous layer with a thickness of 4.0 mm, a solid layer with a thickness of 0.5 mm | 49.0 g | $\Delta W = -14.4$ g($\Delta$\$7.1/shell) |
| No. 4, 50 mm shell | entirely porous solid seat body with a thickness of 5.0 mm | 24.3 g | $\Delta W = -39.1$ g($\Delta$\$19.55/shell) |

The outer surface of the outer layer 1022 of the dome 102 is arcuate surface, and its specific shape matches the acetabulum of the human body. Preferably, the outer surface of the outer layer 1022 of the dome 102 is a spherical surface. The outer surface of the outer layer 1022 of the porous structure of the dome 102 can have spike structures 1029 distributed on it. Preferably, the spikes are integrally formed on the outer surface of the outer layer 1022 of the dome 102 by 3D printing. The distance D between two adjacent spikes may be 300 μm~1000 μm. Preferably, the distance D between two adjacent spikes may be 400 μm~800 μm. The angle α between the spike and the outer surface of the outer layer 1022 of the dome 102 is 65°~110°, that is, the angle between the central axis of the spike and the tangent to the outer layer 1022 of the dome 102 at the location of the spike is 65°~110°. By providing the spikes on the outer surface of the dome 102, the friction coefficient of the artificial acetabular cup can be greatly improved.

The spikes can be generated by cutting grooves in the outer surface of the digital porous structure via software, and the thickness and the height of the spikes can be controlled by adjusting the pitch of the grooves and the depth of the grooves. For porous structure spherical surfaces, the pitch of the spikes can be adjusted by adjusting the dimensions of grooves along the longitude and latitude directions; the height of the spikes can controlled by adjusting the depth of the grooves in the radius direction of the spherical surface. For the porous plane of the cube, the pitch of the spikes can be adjusted by adjusting the width of grooves; the height of the spikes can be controlled by adjusting the depth of grooves. The cube sample has a surface extending in a plane, and the friction coefficient thereof is easier to measure than a spherical surface. Table 2 below shows the measured static friction coefficients and dynamic friction coefficients of five different cubic samples, wherein No. P-00250 is a sample with spikes on the outer surface of the porous structure, the height of the spike is 0.5 mm and the pitch of the spike is 0.5 mm. Wherein No. P-00248 sample has a spike with a height of 0.25 mm and a pitch of 0 mm. No. P-00249 sample has a spike with a height of 0.5 mm and a pitch of 0 mm. No.

P-00250 sample has a spike with a height of 0.5 mm and a pitch of 0.7 mm. No. P-00250EDM side sample is cut in the porous surface with electric spark, and the surface has no spikes, that is, the sample has a spike with a height of 0 mm and a pitch of 0 mm.

TABLE 2

Friction test data

| Operating data | Sample ID P-00248 | | Sample ID P-00249 | | Sample ID P-00250 | | Sample ID P-00251 | | Sample ID P-00250 EDM side | |
|---|---|---|---|---|---|---|---|---|---|---|
| | static | dynamic | static | dynamic | static | dynamic | static | dynamic | static | dynamic |
| 1 | 0.390 | 0.257 | 0.637 | 0.349 | 1.389 | 1.050 | 0.999 | 0.677 | 0.403 | 0.322 |
| 2 | 0.387 | 0.263 | 0.665 | 0.316 | 1.091 | 0.781 | 1.000 | 0.681 | 0.381 | 0.274 |
| 3 | 0.385 | 0.263 | 0.639 | 0.337 | 1.109 | 0.861 | 0.969 | 0.621 | 0.323 | 0.195 |
| 4 | 0.410 | 0.301 | 0.621 | 0.340 | 1.011 | 0.820 | 0.963 | 0.607 | 0.339 | 0.227 |
| 5 | 0.360 | 0.187 | 0.610 | 0.331 | 1.231 | 0.806 | 0.984 | 0.723 | 0.355 | 0.269 |
| mean | 0.386 | 0.254 | 0.634 | 0.335 | 1.166 | 0.864 | 0.983 | 0.662 | 0.360 | 0.257 |
| Minimum | 0.360 | 0.187 | 0.610 | 0.316 | 1.011 | 0.781 | 0.963 | 0.607 | 0.323 | 0.195 |
| Maximum | 0.410 | 0.301 | 0.665 | 0.349 | 1.389 | 1.050 | 1.000 | 0.723 | 0.403 | 0.322 |
| standard deviation | 0.016 | 0.037 | 0.019 | 0.011 | 0.132 | 0.097 | 0.015 | 0.042 | 0.029 | 0.043 |

It can be seen from the table that the static friction coefficient and the dynamic friction coefficient of the porous structure surface provided with the spike structures are much greater than the static friction coefficient and the dynamic friction coefficient of the porous structure surface without the spike structure. Therefore, it is more beneficial to the mutual fit and cooperation of the implant and the human bone, resulting in the pinning effect. It should be understood that in the embodiment shown in FIGS. 1-2, the spike structures are not necessarily be provided on the porous structure of the outer layer.

Figure 3:
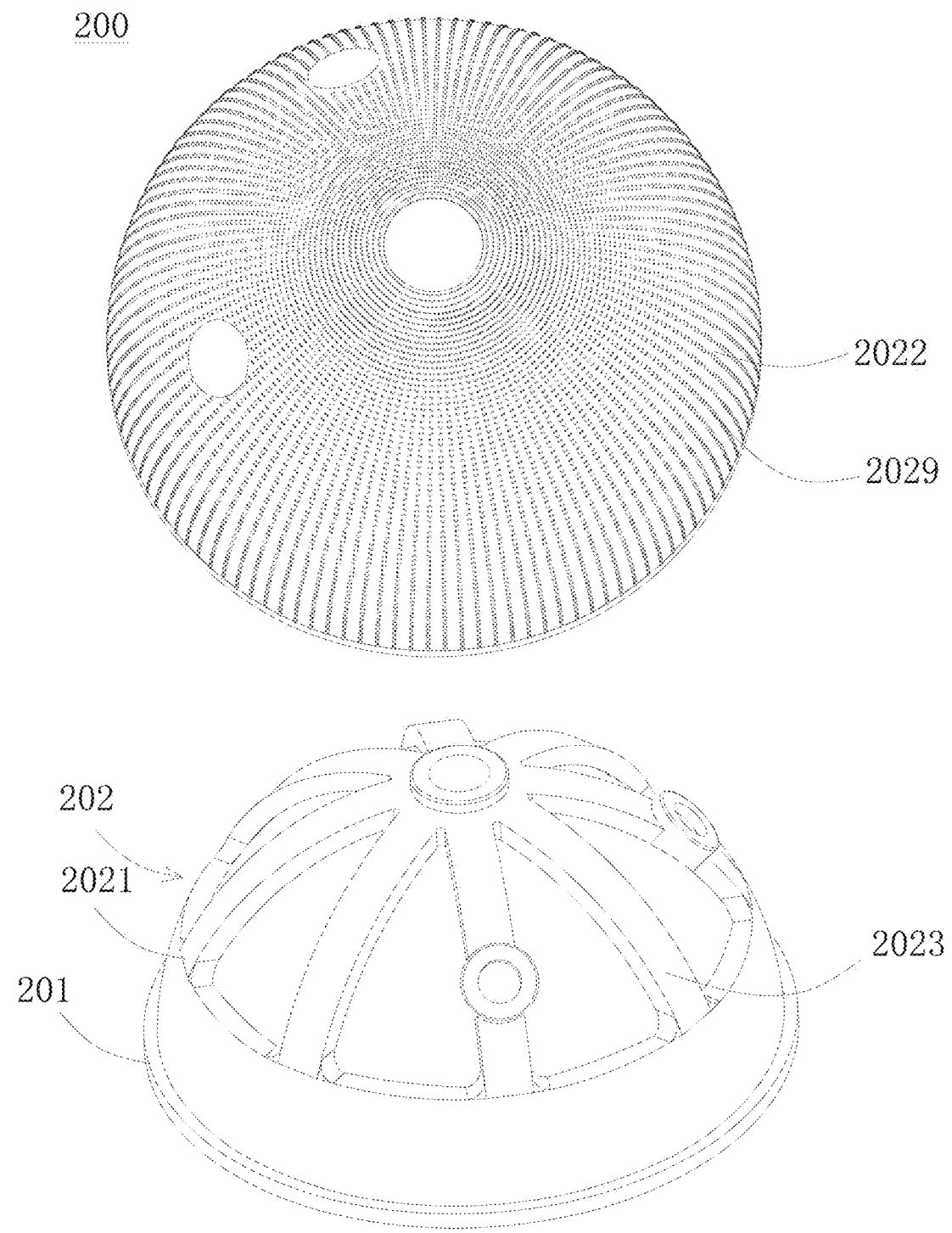
FIG. 3 is an exploded perspective view of an artificial acetabular cup according to another embodiment of the present invention.

FIG. 3 shows an exploded perspective view of an artificial acetabular cup 200 of the second embodiment of the present invention. The main difference between this embodiment and the embodiment shown in FIG. 1 is that the inner layer of the dome of the artificial acetabular cup 200 of this embodiment is entirely a solid layer. As shown in FIG. 2, the artificial acetabular cup 200 has an annular base 201 and a dome 202. The structure of the annular base 201 can be the same or substantially the same as the embodiment shown in FIG. 1, and will not be described in detail here. The dome 202 has an inner layer 2021 and an outer layer 2022. In this embodiment, the inner surface of the inner layer 2021 of the dome 202 of the artificial acetabular cup 200 is a solid layer and has a smooth surface, that is, no protruding beams. It should be understood that the inner surface of the inner layer 2021 can also be provided with some protruding beams. Similarly, the outer surface of the inner layer of the dome 202 of the artificial acetabular cup 200 can be provided with a protruding beam 2023, as shown in FIG. 2. Like the embodiment shown in FIG. 1, the outer layer 2022 of the artificial acetabular cup 200 of this embodiment is a porous structure layer, which integrally covers the inner layer 2021.

The artificial acetabular cup 200 of the type shown in FIG. 3 is generally suitable for super large hip cups, such as artificial acetabular cups of 60 mm, 62 mm, 64 mm, 66 mm, 67 mm, 70 mm, 72 mm, 74 mm, 76 mm, 78 mm, 80 mm and other specifications. A super large artificial acetabular cup with this structure will have high rigidity and low weight, and at the same time, will render the UHMWPE lining thinner.

Figure 4:
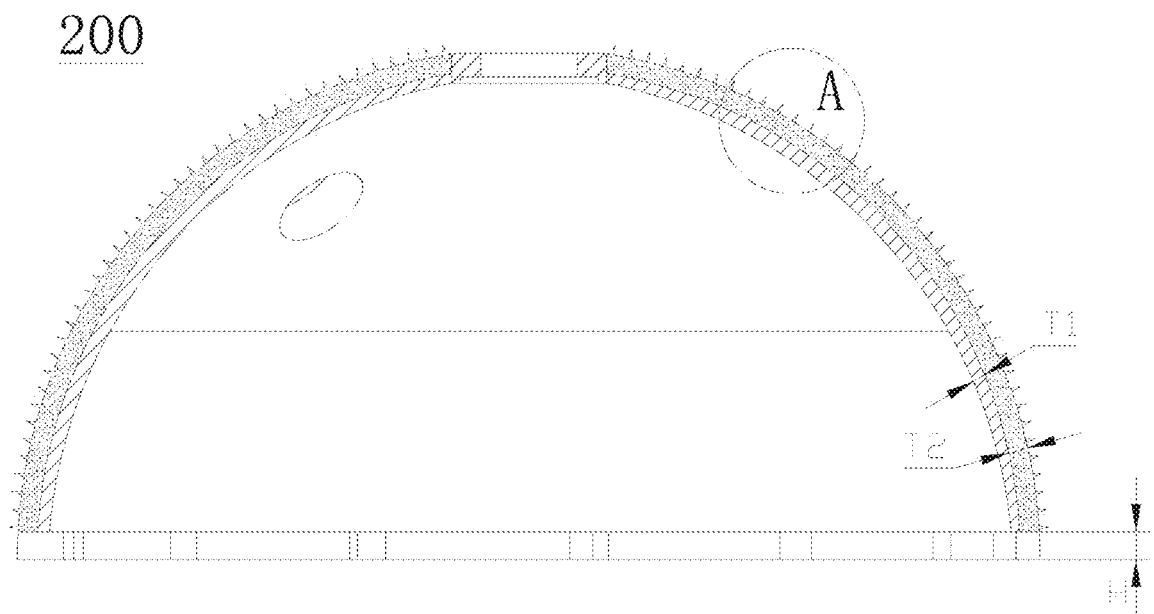
FIG. 4 is a cross-sectional view of the artificial acetabular cup of FIG. 3.
Figure 5:
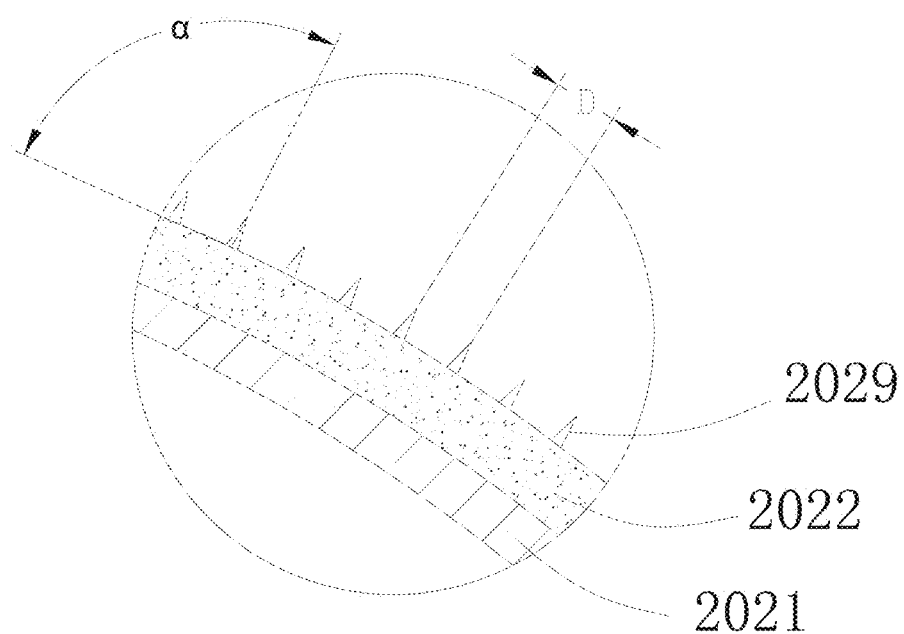
FIG. 5 is an enlarged view of part A of FIG. 4.
Figure 6:
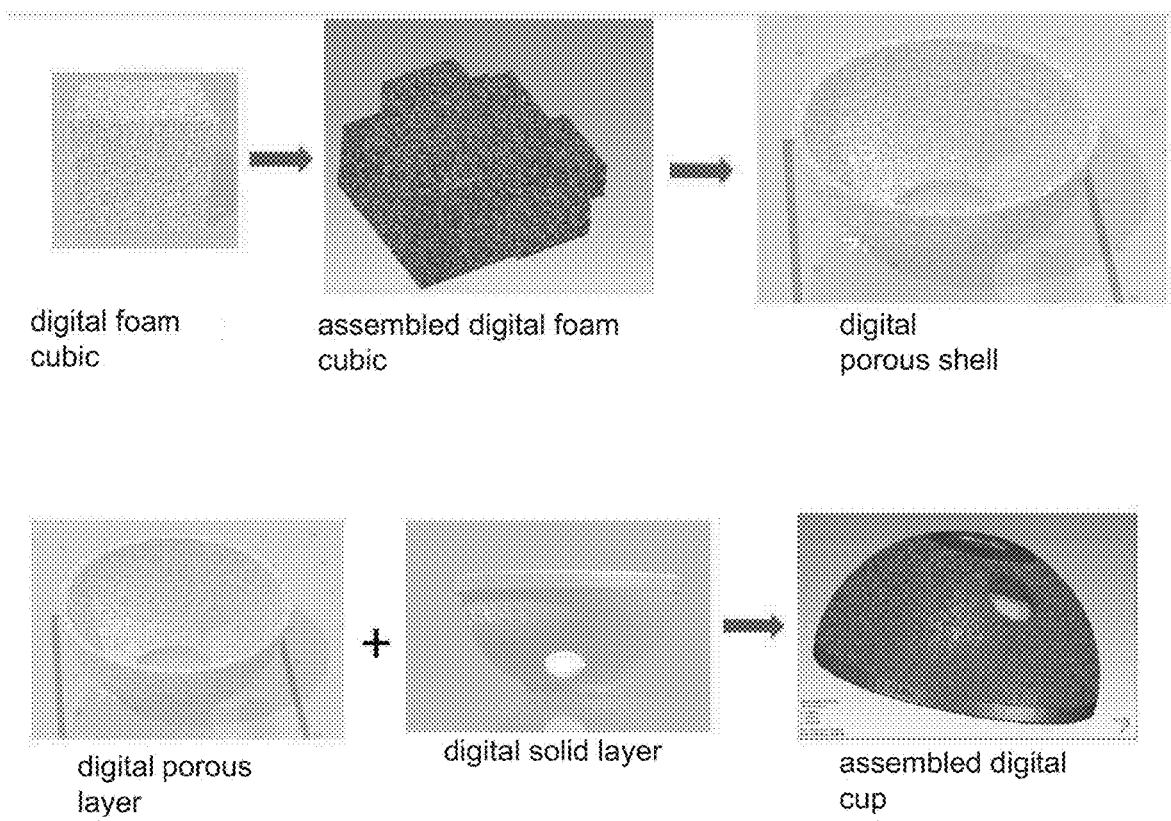
FIG. 6 is a flowchart of a method for manufacturing an orthopedic implant according to an embodiment of the present invention.
Figure 7:
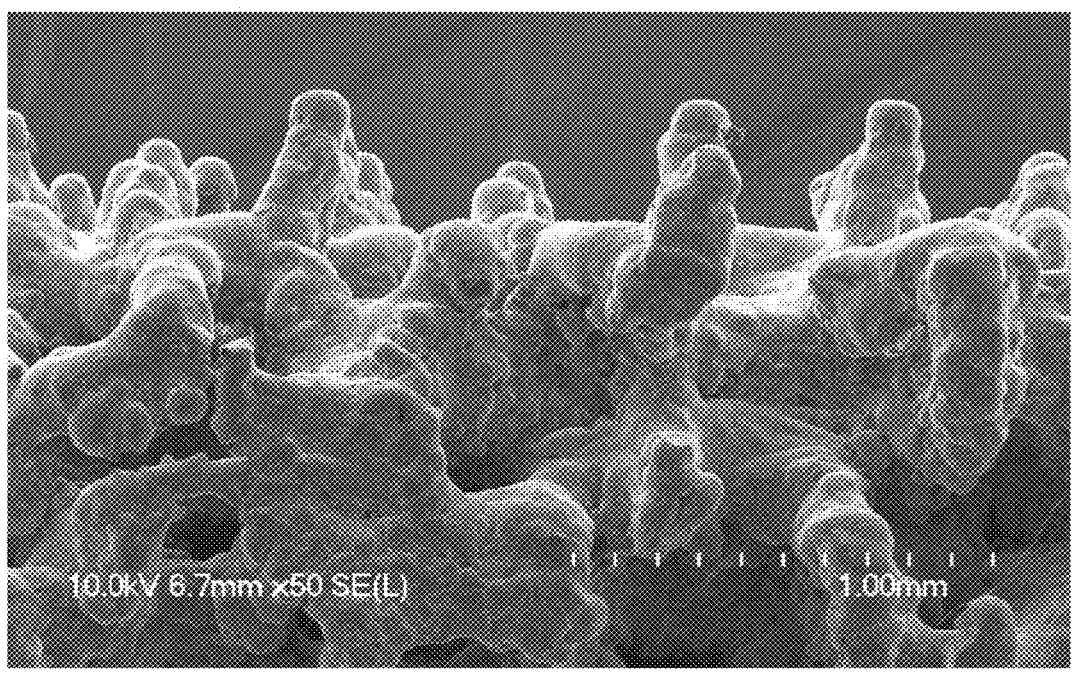
FIGS. 7~10 are microscope images of a variety of different spike structures on the porous structure surface of an orthopedic implant manufactured according to the manufacturing method of FIG. 6.
Figure 8:
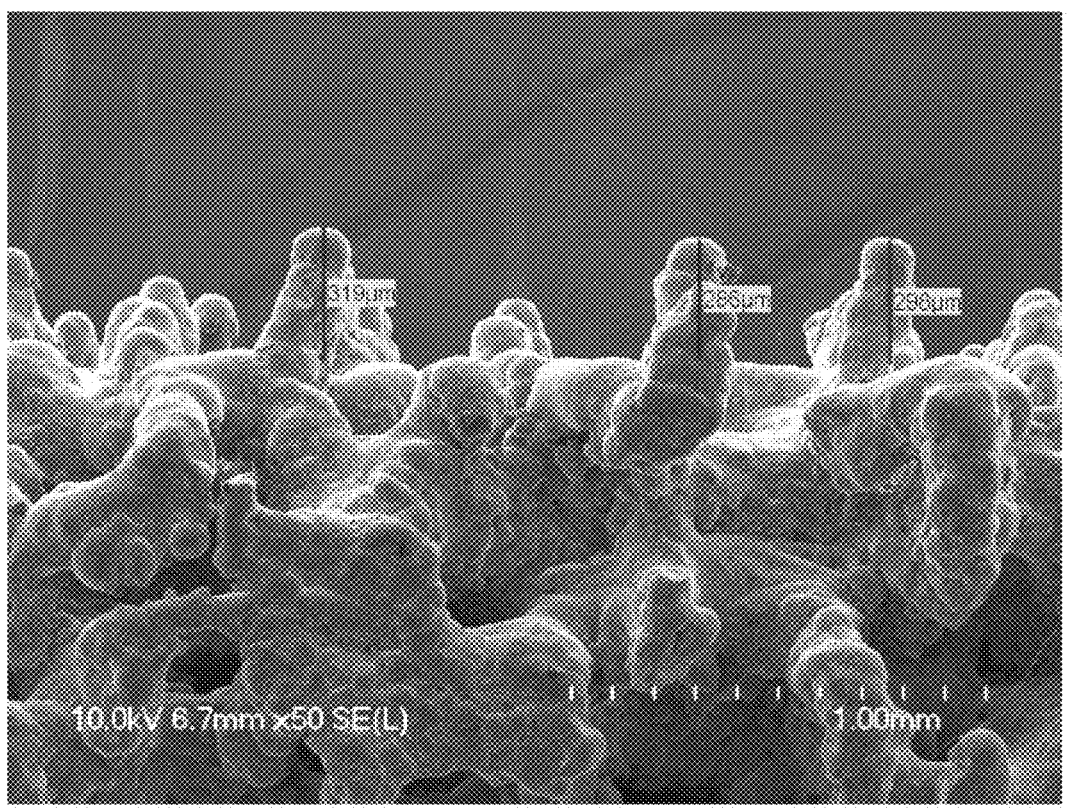
Figure 9:
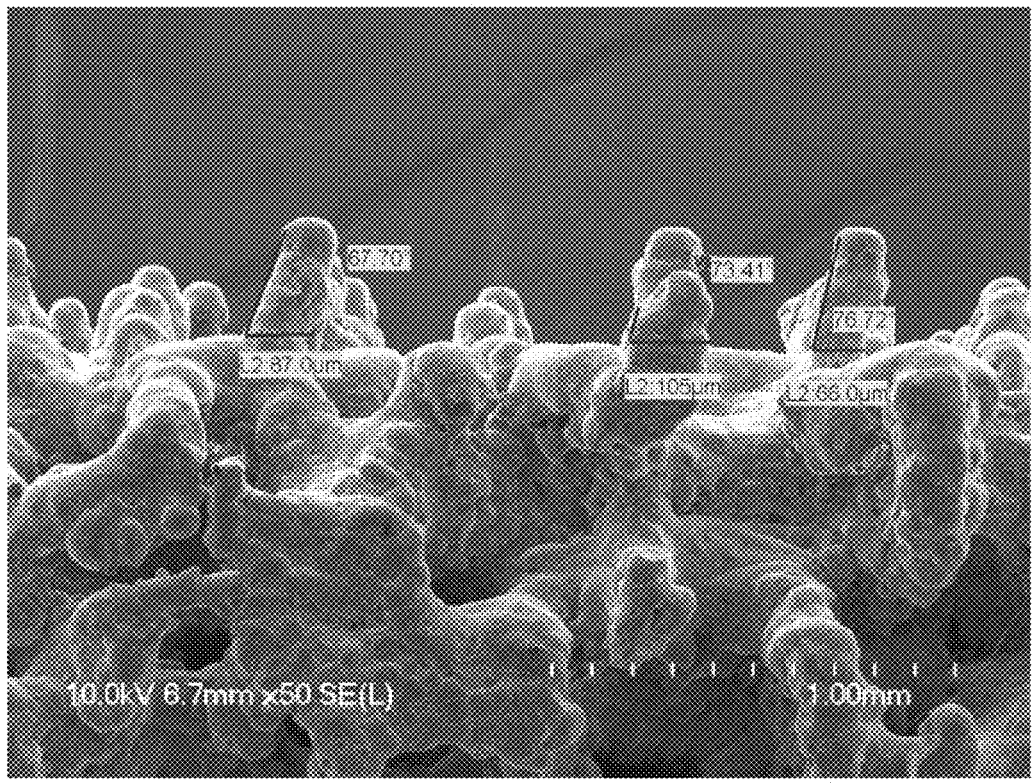
Figure 10:
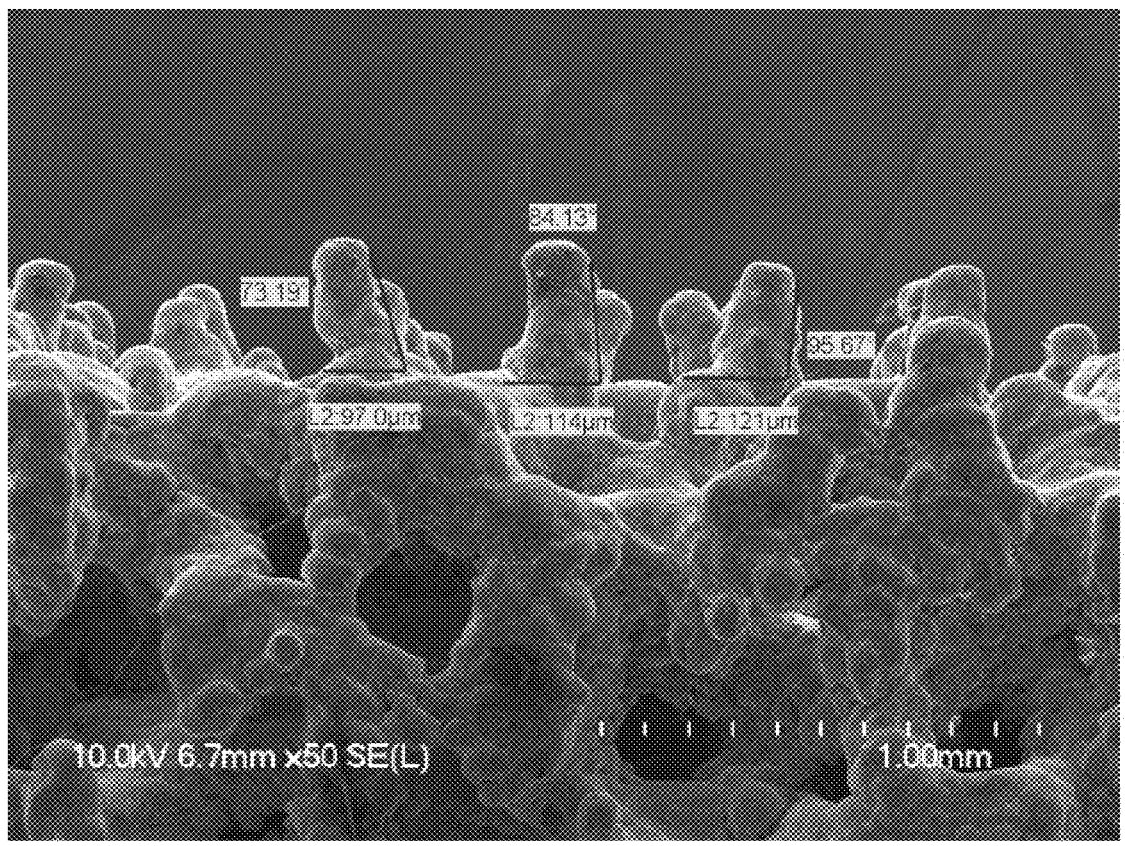

Spike structures 2029 are distributed on the outer surface of the outer layer 2022 of the dome 202 of the artificial acetabular cup 200, as shown in FIGS. 4-5. The spikes 2029 are integrally formed on the outer surface of the outer layer 2022 of the dome 202 by 3D printing. The distance D between two adjacent spikes may be 300 μm~1000 μm. Preferably, the distance D between two adjacent spikes may be 400 μm 800 μm. The angle α between the spike and the outer surface of the outer layer 2022 of the dome 202 is 65°~110°, that is, the angle between the central axis of the spike and the tangent to the outer layer 2022 of the dome 202 at the location of the spike is 65°~110°. By providing the spike on the outer surface 2022 of the dome 202, the friction coefficient of the artificial acetabular cup 200 can be greatly improved. It should be understood that in the embodiments shown in FIGS. 3-5, the spike structure can not be provided on the porous structure of the outer layer 2022.

The aforementioned artificial acetabular cup can be made of titanium alloy, pure titanium, cobalt-chromium alloy, or stainless steel. Preferably, the artificial acetabular cup can be formed by 3D printing. Specifically, as shown in FIG. 5, during manufacturing, a digital model of an artificial acetabular cup is firstly built, which has the same structure as the artificial acetabular cup to be manufactured. Any suitable method known in the art or to be developed can be used to build the above-mentioned digital model of the artificial acetabular cup. Then, the digital model of the artificial acetabular cup will be 3D printed, thereby obtaining the artificial acetabular cup.

The inventor further found that the above-mentioned structure of the outer layer of the dome, that is, the structure with spikes distributed on the porous substrate, can also be applied to other orthopedic implants, such as artificial knee joints, wrist joints, elbow joints, finger joints, and condyle joints. Specifically, the present application also develops an orthopedic implant having a porous structure body, which has a substrate and a plurality of spikes. The plurality of spikes protrude from and are distributed on the outer surface of the substrate. The substrate is a porous structure, and its outer surface may be flat, curved or any suitable shape. Preferably, the substrate is a reticulated porous structure. The reticulated porous structure can be obtained by scanning the reticulated artificial foam or the reticulated structure of human bone etc. The spikes may be cones, cylinders, or irregular protrusions etc. The distance D between two adjacent spikes is 300 μm~1000 μm. The angle between the spike and the outer surface of the substrate is 65°~110°.

The porous structure is made of titanium alloy, pure titanium, cobalt-chromium alloy or stainless steel etc. The porous structure is made by 3D printing. In an embodiment of the present application, the manufacturing method of the orthopedic implant may comprise the following steps:

S1 building a digital model of a porous substrate;

S2 adding a digital model of a spike to the digital model of the porous substrate, resulting in the digital model of the spike and the digital model of the porous substrate overlapping;

S3 arraying the digital model of the spike to obtain a plurality of digital models of the spike;

S4 merging the plurality of digital models of the spike obtained by arraying with the digital model of the porous substrate, and then performing 3D printing to obtain the orthopedic implant.

The above-mentioned step S1 can be implemented through the following sub-steps:

S11 scanning the reticulated artificial foam and saving the scanning results as a digital porous model;

S12 editing the digital porous model;

S13 assembling the digital porous model to form a digital porous block;

S14 editing the digital porous block to obtain a digital model of the porous substrate.

Further, the manufacturing method further comprises the following steps: before performing 3D printing, further merging a digital model with a digital model of a porous foam, wherein the porous model is obtained by merging the plurality of digital models of the spike obtained by arraying with the digital model of the substrate. Preferably, the merging of the plurality of digital models of the spike obtained by arraying with the digital model of the substrate is performed by Boolean operation.

The above-mentioned manufacturing method of the orthopedic implant may further comprise building a digital model of a solid substrate, further merging a first digital model obtained by merging the plurality of digital models of the spike obtained by arraying with the digital model of the substrate with the digital model of the solid substrate to obtain a second digital model. Next, editing the second digital model to obtain a third digital model with the desired shape of the orthopedic implant. Finally, editing the above-mentioned third digital model to obtain the desired orthopedic implant. The orthopedic implant may be an artificial knee joint, artificial hip joint, wrist joint, elbow joint, finger joint, condyle joint, etc.

The orthopedic implant manufactured by the above-mentioned method can match human bones well, promote bone growth, and has a low production cost.

The preferred embodiments of the present invention have been described in detail above, but it should be understood that, if necessary, aspects of the embodiments can be modified to adopt aspects, features, and concepts of various patents, applications, and publications to provide additional embodiments.

Considering the detailed description above, these and other changes can be made to the embodiments. Generally speaking, in the claims, the terms used should not be considered as limited to the specific embodiments disclosed in the specification and claims, but should be understood as including all possible embodiments together with all equivalent scope of the claims.

The invention claimed is:

1. An artificial acetabular cup having an annular base and a dome extending from the annular base, wherein the dome has an inner layer and an outer layer covering the inner layer, at least a part of the inner layer of the dome is a solid layer, at least a part of the outer layer of the dome is a porous structure layer, and a thickness of the inner layer is less than that of the porous structure layer of the outer layer;

wherein the inner layer of the dome has a plurality of solid beams extending between the annular base and a top of the dome in a longitude direction, the plurality of solid beams is spaced apart from each other in a latitude direction, and the porous structure layer is arranged between two adjacent solid beams, and an outer surface of the dome is provided with the porous structure layer.

2. The artificial acetabular cup according to claim 1, wherein at least a part of the inner layer of the dome is a porous layer, and the porous layer of the inner layer of the dome is concave relative to the solid beam.

3. The artificial acetabular cup according to claim 1, wherein the entire outer layer of the dome is the porous structure layer.

4. The artificial acetabular cup according to claim 1, wherein the thickness of the inner layer is $1/50$~$1/2$ of that of the outer layer.

5. The artificial acetabular cup according to claim 1, wherein at least one of the plurality of solid beams is provided with a mounting hole.

6. The artificial acetabular cup according to claim 1, wherein the dome has a solid cylindrical portion integrally extending from an upper end surface of the annular base and the plurality of solid beams extends from the solid cylindrical portion in the longitudinal direction of the dome.

7. The artificial acetabular cup according to claim 1, wherein an outer surface of the outer layer of the dome is distributed with spikes.

8. The artificial acetabular cup according to claim 7, wherein the spike is integrally formed on the outer surface of the outer layer of the dome.

9. The artificial acetabular cup according to claim 7, wherein a distance between two adjacent spikes is 300 μm-1000 μm.

10. The artificial acetabular cup according to claim 7, wherein an angle between a central axis of the spike and a tangent to the outer surface of the outer layer of the dome is 65°-110°.

11. The artificial acetabular cup according to claim 1, wherein an outer surface of the outer layer of the dome is arcuate surface.

12. The artificial acetabular cup according to claim 1, wherein the artificial acetabular cup is formed by 3D printing.

13. The artificial acetabular cup according to claim 1, wherein the artificial acetabular cup is made of titanium alloy, pure titanium, cobalt-chromium alloy, or stainless steel.

* * * * *